US008691150B2

(12) United States Patent
Lorenz et al.

(10) Patent No.: US 8,691,150 B2
(45) Date of Patent: Apr. 8, 2014

(54) SYSTEM FOR DETERMINING A NUMBER OF UNUSED CONSUMABLE ELEMENTS FOR TESTING A BODILY FLUID SAMPLE

(75) Inventors: Robert Lorenz, Worms (DE); Kai-Oliver Schwenker, Hassloch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/303,825

(22) Filed: Nov. 23, 2011

(65) Prior Publication Data
US 2012/0301362 A1 Nov. 29, 2012

(30) Foreign Application Priority Data

Dec. 4, 2010 (EP) .................................... 10015313

(51) Int. Cl.
*G01N 21/00* (2006.01)
*G01N 31/00* (2006.01)
*G01N 33/00* (2006.01)
*A61J 1/06* (2006.01)
*B01L 3/00* (2006.01)
*G01N 21/75* (2006.01)
*G01N 31/22* (2006.01)
*G01N 33/52* (2006.01)
*G01N 35/00* (2006.01)
*A61B 5/00* (2006.01)

(52) U.S. Cl.
USPC ............. 422/66; 422/400; 422/401; 422/402; 422/403; 422/404; 422/554; 600/583

(58) Field of Classification Search
USPC .............................. 422/401–403, 66; 600/583
See application file for complete search history.

(56) References Cited

U.S. PATENT DOCUMENTS

| 4,954,319 A * | 9/1990 | Koizumi et al. ................. 422/67 |
| 6,603,887 B1 | 8/2003 | Focke et al. |
| 2002/0188224 A1 | 12/2002 | Roe et al. |
| 2005/0232815 A1 * | 10/2005 | Ruhl et al. ...................... 422/66 |
| 2006/0216817 A1 | 9/2006 | Hoenes et al. |
| 2007/0020143 A1 * | 1/2007 | Seidenstricker et al. ....... 422/56 |
| 2007/0119710 A1 | 5/2007 | Goldberger et al. |
| 2007/0217950 A1 | 9/2007 | Kramer et al. |
| 2011/0243810 A1 | 10/2011 | Schosnig et al. |

FOREIGN PATENT DOCUMENTS

| EP | 2177914 A1 | 4/2010 |
| WO | 2005/032372 A1 | 4/2005 |

* cited by examiner

*Primary Examiner* — Jill Warden
*Assistant Examiner* — Julie Tavares
(74) *Attorney, Agent, or Firm* — Roche Diagnostics Operations, Inc.

(57) ABSTRACT

The invention relates to a system for testing a sample of bodily fluid, comprising a carrier band, which carries a plurality of consumable elements, wherein one end of the carrier band is attached to a wind-up device for winding the carrier band, together with used consumable elements, onto a reel for the band transport, and comprising a display for displaying information regarding the supply of yet unused consumable elements of the carrier band. According to the invention, it is provided that information regarding the supply of yet unused consumable elements of the carrier band is obtained from an angle of rotation and from a band transport length by which the carrier band is moved with a rotation of the reel about said angle of rotation.

16 Claims, 4 Drawing Sheets

SYSTEM FOR DETERMINING A NUMBER OF UNUSED CONSUMABLE ELEMENTS FOR TESTING A BODILY FLUID SAMPLE

CLAIM OF PRIORITY

The present application is based on and claims priority to European Patent Application No. 10015313.9, filed Dec. 4, 2010, which is hereby incorporated by reference in its entirety.

TECHNICAL FIELD OF THE INVENTION

The present application relates to systems for testing bodily fluid samples, and more particularly to such systems comprising devices having bands for carrying consumable elements to receive and test the bodily fluid samples, and more particularly to the transport of such bands and detection and display of information relating to such transport.

BACKGROUND

Systems comprising a device, such as a cartridge or cassette, that transports a tape or carrier band of consumable elements for testing bodily fluid samples offer a high degree of user comfort, because a large number of consumable elements, for example, test fields for determining glucose concentration, can be disposed on a carrier band. As a result, exchanging a band cartridge in a measuring device, which many users find troublesome, is necessary only infrequently.

A rewritable data storage medium, for example, an RFID, can be attached to such band cartridges, on which the number of unused consumable elements that remain is stored. This number can then be updated by a measuring device into which the cartridge is inserted, each time a consumable element is used. In this way, the number of consumable elements still available in a cartridge can be reliably monitored and displayed to a user when the supply is running low. Disadvantageous in this case are the costs associated with the data storage medium.

An object of the present invention is therefore that of revealing a more cost-effective method for obtaining information regarding the number of unused consumable elements of a carrier band remaining in the supply thereof, so that a user will not be surprised by the need to replace a band cartridge.

SUMMARY

This object and others that will be appreciated by a person of ordinary skill in the art have been achieved according to the embodiments of the present invention disclosed herein. In one embodiment, the present invention comprises a system in which information regarding the size of the supply of unused consumable elements of the carrier band is obtained from an angle of rotation and a band transport length by which the carrier band is moved with a rotation of the reel about said angle of rotation. In this way, it can be determined how far the reel needs to rotate, i.e., about what angle, in order for the carrier band to move forward along a predefined transport length. The predefined transport length can correspond to the distance between two consumable elements, for example, or to the distance between markings applied to the carrier band, which are guided past a sensor during band transport.

More specifically, the transport movement of the carrier band effected by a full rotation of the reel is greater the thicker the reel is. With a rotation about a predefined angle, the carrier band is moved forward by a greater band transport length, the greater the diameter of the reel is. Because the thickness of the reel is greater, the greater the band length is that has already been wound onto it, by analyzing the angle of rotation associated with a band transport length, information regarding the band length that has already been wound up, and therefore regarding the number of consumable elements that have already been used, can be obtained. More specifically, the band length that has already been wound up by the wind-up device is a measure of the number of consumable elements that have already been used. Accordingly, the remaining band length is proportional to the number of consumable elements that are still available for use.

Therefore, when the thickness of the reel, particularly the diameter thereof, exceeds a critical threshold, this means that the supply of unused consumable elements remaining will soon be exhausted. Rather than directly measuring the thickness of the reel, or continuously adding up the lengths of the band sections that are wound up each time the reel device is actuated, according to the invention, a conclusion regarding the thickness of the reel is drawn from the forward movement of the band associated with an angle of rotation, and thereby, information regarding the supply of yet unused consumable elements of the carrier band is obtained. More specifically, the forward movement of the band resulting from a specific angle of rotation is a measure of the percentage of a supply of consumable elements, provided on a carrier band, which have already been used.

From the angle of rotation and the band transport length by which the carrier band is moved with a rotation of the reel about said angle of rotation, the precise number of consumable elements that have already been used can be determined. If the number of consumable elements carried by a carrier band is known, which is usually the case, then the number of unused consumable elements remaining can also be calculated. However, in order to notify a user in good time that the supply of consumable elements will soon run out, it is not absolutely necessary to determine the precise number of unused consumable elements that remain. Instead it is generally sufficient to provide an approximate indication, for example, with an inaccuracy of up to 3 consumable elements or up to 10% referred to the total number of consumable elements in a fresh carrier band.

Information regarding the size of the supply of yet unused consumables of the carrier band, e.g. the number of unused consumable elements of the carrier band remaining in the supply thereof, may also be displayed to a user, for example, by generating a warning signal, e.g. a light signal, as soon as the thickness of the reel exceeds a critical threshold value. It is also possible, in particular, to indicate the size of the supply of yet unused consumable elements of the carrier band as a bar, the length of which correlates to the number of unused consumable elements that remain, in other words, said bar is shorter, the fewer unused consumable elements remain.

One refinement of the invention provides that the carrier band has markings disposed at regular intervals, and the markings are detected by a sensor for the purpose of measuring the band transport length, in other words, the forward movement of the band. Optical sensors, for example, photodiodes, phototransistors, or other photosensitive sensors are particularly well suited for this purpose.

For detecting markings, a measuring spot on the carrier band can be illuminated by a light source, and this measuring spot can be monitored by a sensor. When a marking moves through the measuring spot, the brightness detected by the sensor changes, and therefore, the marking can be detected.

In the simplest case, the markings can be embodied as holes or recesses in the carrier band with light source and sensor being disposed on different sides of the carrier band. The detection of a marking then functions according to the principle of a photoelectric barrier. In other embodiments, the markings can be detected via reflection. For this purpose, it is favorable for the markings to differ in terms of their reflectivity as much as possible from the remaining regions of the carrier band, in other words, to form the clearest possible contrast. Bright surfaces or metal coatings are highly reflective and therefore contrast highly with dark, particularly black regions. The term reflection in this case is being used in its general meaning, and therefore also covers reflectance, i.e., non-directional or diffuse reflections, and remission of light at other wavelengths. Fluorescent pigments or fluorescent dyes can also be used for the position markings, for example.

In yet other embodiments, stop markings can be provided on the carrier band, and the detection of said markings by the sensor causes the wind-up device to stop such that a consumable element is positioned in a position of use, for example, a test field can be placed in a position for collecting a sample. Additional markings can be provided on the carrier band, in order to also enable a simple measurement of the band travel speed or of a band transport length between two stop markings.

A further refinement of the invention provides for the wind-up device to be controlled on the basis of the obtained information regarding the size of the supply of yet unused consumable elements of the carrier band thereof. By supplying the information regarding the supply of unused consumable elements, e.g. the number of unused consumables that remain, to a control device, the rotational speed of the wind-up device for the purpose of band transport can be adjusted to the thickness of the reel. In this manner, the time required for providing another consumable element can be made largely independent of reel thickness. Therefore, using the obtained information regarding the supply of unused consumable elements, the wind-up device can be controlled in such a way that a target value for the time required to provide another consumable element is predefined.

For example, as a consumable element is being provided, a band travel speed can be regulated to a target value that is independent of the thickness of the reel. The band travel speed during provision of a consumable element is understood as an average band travel speed, because the carrier band is first accelerated at the start of a transport movement, and is then decelerated. The band travel speed during provision of a consumable element is the quotient of the distance between two consumable elements and the time required to transport the band over the corresponding path length.

Some users might find it irritating that the time required for providing a consumable element is subject to severe fluctuations, depending on the thickness of the reel. This can be remedied by adding a control device to the system, for the purpose of regulating the band travel speed to a target value that is independent of the thickness of the reel. For such regulation, it is not absolutely essential for information regarding the size of the supply of unused consumable elements of the carrier band to be determined and displayed. For example, it is sufficient for the band transport speed at any given moment to be constantly monitored using markings applied to the carrier band, and, if necessary, to increase or decrease the rotational speed of the reel such that a consumable element is provided within the desired target time, in other words, said element reaches its position of use, for example, for sample collection or concentration measurement. One aspect of the invention, which can also have independent significance, therefore relates to a system for testing a sample of bodily fluid, comprising a carrier band, which carries multiple consumable elements, wherein one end of the carrier band is attached to a wind-up device for winding the carrier band, together with used consumable elements, onto a reel for the purpose of band transport, and comprising a control device for regulating the band travel speed to a target value that is independent of the thickness of the reel.

The obtained information regarding the supply of unused consumable elements of the carrier band can be stored in a memory. If the wind-up device is to be controlled such that the time required for providing another consumable element remains constant, the wind-up device, when actuated, can be actuated immediately, taking into consideration the corresponding information. When a consumable element is used, the stored counter status can be updated, in other words, it can be adjusted by one, for example, the counter status can indicate the number of usable consumable elements that remain, and this number can be decreased by one with each use.

A further refinement of the invention provides for the band transport length to be detected on the basis of the rotational angle position of the reel, from which a value for the imbalance of the reel is determined, and, based upon this value, a fresh carrier band, which carries only unused consumable elements, is distinguished from a carrier band that has already been partially wound up, and which carries at least one used consumable element. Test fields and other consumable elements, which extend in the longitudinal direction of the carrier band and are less flexible than the carrier band, can cause a substantial imbalance of the reel as it is being wound up.

As a result of this imbalance, the band transport length is dependent not only on the angle of rotation of the reel, but also on the rotational angle position thereof. With a fresh carrier band, usually no consumable elements have yet been wound onto the wind-up device, and consequently, there is no imbalance. Therefore, a fresh carrier band can be detected on the basis of the absence of an imbalance. On this basis, a system according to the invention can automatically detect when a new band cartridge, which contains a fresh carrier band, is inserted into a measuring device. A determined value for the imbalance of the reel can be stored in a memory. If, at a later time, a changed value for imbalance is detected, this can be identified as a replacement of the carrier band. It is even possible to detect a case in which a used or partially used carrier band is replaced by a carrier band that has already been partially wound up, in other words, one that also carries used consumable elements.

The consumable elements are typically test elements for measuring an analyte concentration in a sample of bodily fluid. Test elements of this type generally contain test reagents, which cause a test reaction when they come into contact with a sample of bodily fluid. In particular, test reactions for the photometric or electrochemical assay of an analyte concentration, for example, glucose concentration or lactate concentration, are commonly used. The consumable elements can also involve piercing elements, for example. Carrier bands that carry piercing elements and test elements disposed between the piercing elements, and carrier bands that carry piercing elements with integrated test elements, and carrier bands that carry exclusively piercing elements are all possible in this connection.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
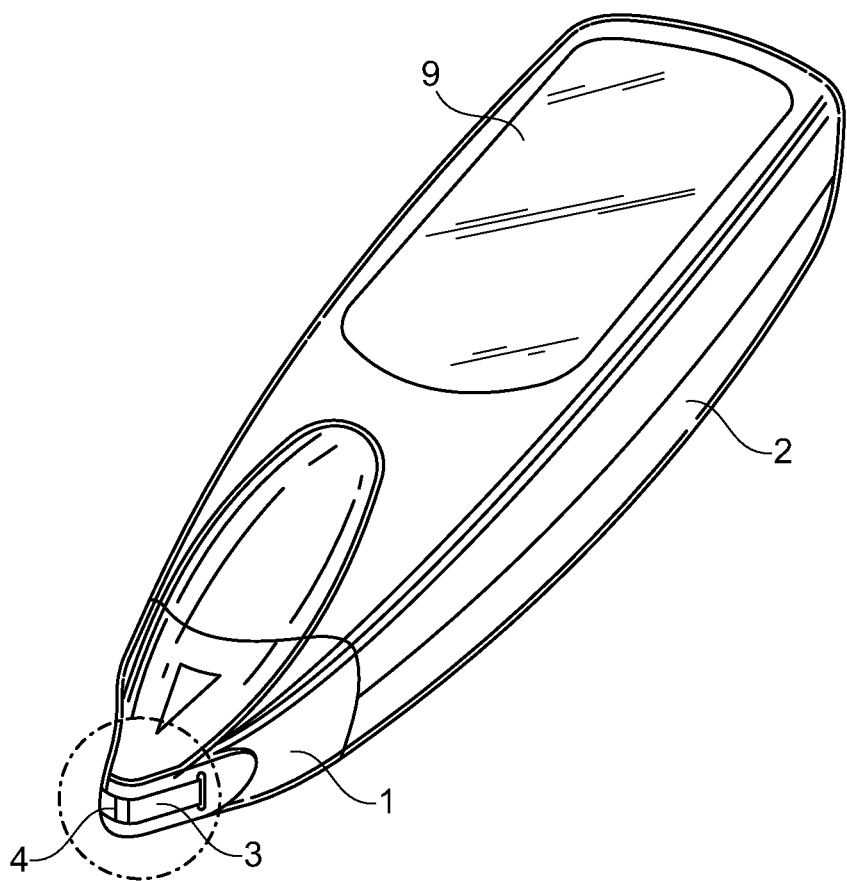
FIG. 1 shows a schematic illustration of a system for testing a sample of bodily fluid.

FIG. 1 shows a system for measuring an analyte concentration of a sample of bodily fluid, for example, for measuring the glucose concentration of blood and/or interstitial fluid. Systems of this type are required by diabetics, for example, who must measure their blood sugar concentration several times daily. The system 1 illustrated here comprises, as the first system component, a band cartridge 1 illustrated in FIG. 2, and as a further system component, a hand-held device 2. In FIG. 1, the hand-held device 2 is shown with a band cartridge inserted.

Figure 2:
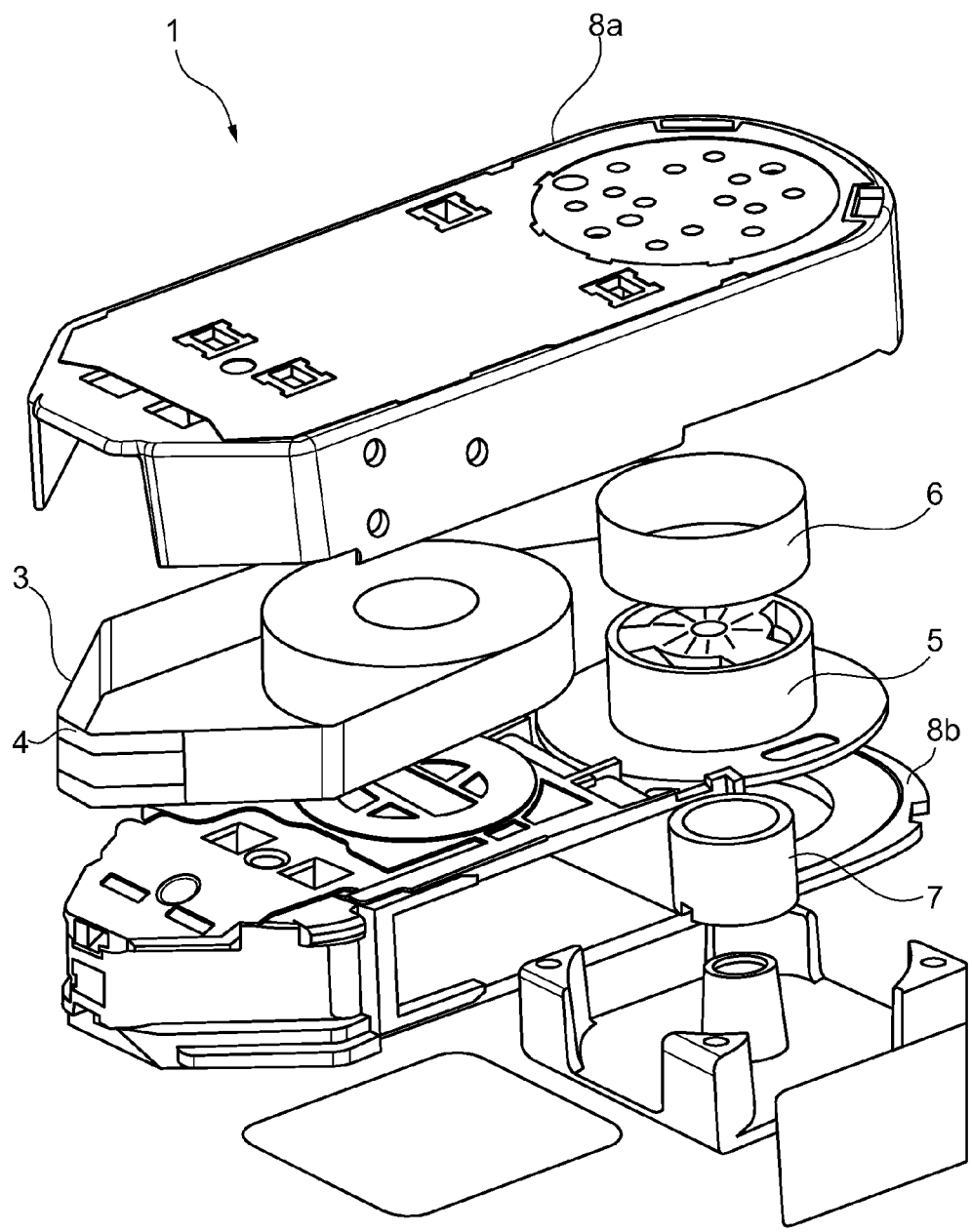
FIG. 2 shows an exploded illustration of an embodiment example of a band cartridge having a carrier band that carries consumable elements.

The band cartridge 1 illustrated in FIG. 2 contains a carrier band 3, which carries consumable elements 4 in the form of test elements. The test elements may be for example, test fields with test reagents, which cause a test reaction, for example, a discoloration that can be photometrically analyzed with regard to an analyte concentration, when said reagents come into contact with a sample of bodily fluid. In FIG. 2, in the interest of clarity, only a single consumable element 4 is shown. Actually, however, the carrier band 3 carries a greater number of test elements, so that for example, up to 50 or even more concentration determinations can be carried out with the carrier band.

One end of the carrier band 3 contained in the band cartridge 1 is attached to a wind-up device 5, such as a winding reel or a pin. For band transport, the carrier band 3 can be wound, together with used consumable elements 4, onto a reel 6 on the wind-up device 5. A section of the carrier band 3 containing unused consumable elements is enclosed inside a housing 8a, 8b of the band cartridge 1, and is wound onto a roll 7 as the supply reel.

The hand-held device 2 illustrated in FIG. 1 has an electrical display 9 for displaying measurement results. The display 9 can also display information regarding the supply of unused consumable elements 4 of the carrier band 3 in a cartridge 1 inserted into the hand-held device 2. For example, the number of unused consumable elements 4 can be displayed, or a warning signal can be displayed, when the supply drops below a critical threshold.

In the illustrated system, the information regarding the supply of unused consumable elements 4 is determined from an angle of rotation and from a band transport length by which the carrier band 3 is moved forward with a rotation of the reel 6 about said angle of rotation. More specifically, the larger the reel 6 is, the farther the carrier band 3 is transported with a rotation of the reel 6 about a defined angle. Because the thickness of the reel 6 is greater the more consumable elements 4 have already been used, information regarding the thickness of the reel and thereby also regarding the supply of unused consumable elements 4 of the carrier band 3 can be obtained from the angle of rotation and from the forward movement of the band, i.e., a band transport length, effected therewith.

The hand-held device 2 contains an analysis unit, not shown here, which is configured for determining the information regarding the supply of unused consumable elements 4 of the carrier band 3 from an angle of rotation and from a band transport length by which the carrier band 3 is moved with a rotation of the reel 6 about said angle of rotation. The analysis unit can receive the angle of rotation from an electric motor, for example, which is provided for driving the wind-up device 5. An additional rotational angle sensor may also be provided, which detects the angle of rotation of the wind-up device 5 or of a shaft that drives the wind-up device.

Figure 3:
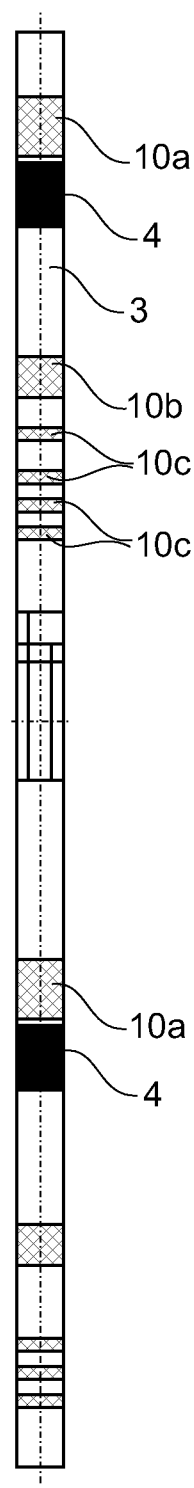
FIG. 3 shows a schematic illustration of an embodiment example of a carrier band with consumable elements and markings.

As illustrated in FIG. 3, the carrier band 3 may carry various markings 10a, 10b, 10c, which can be detected by a sensor of the hand-held device 2, not shown here, for the purpose of measuring band transport length. The markings 10a, 10b, 10c can be applied to the carrier band 3 as black strips, similar to a barcode, for example.

In the embodiment example illustrated in FIG. 3, the markings 10a form stop markings, the detection of which by a sensor, not shown here, of the hand-held device 2 causes the wind-up device 5 to stop. Additional markings 10b, 10c are also provided. Preferably, a greater number of markings 10c are disposed at constant intervals between two test fields 4. Using these markings 10c, the band travel speed can be measured, for example. In the schematic illustration of FIG. 3, only some of the markings 10c are shown. Actually, the carrier band 3 has a substantially greater number of markings between two consumable elements.

Also provided in the illustrated embodiment example is a marking 10b, which precedes a series of markings 10c and can cause an activation of a measuring device of the hand-held device 2, not shown, for a measurement that will soon be carried out, for example.

In one embodiment, the wind-up device 5 is driven by an electric motor. The rotational speed of the wind-up device 5 for band transport is reduced as the number of remaining unused consumable elements 4 of the carrier band 3 decreases. This means that the wind-up device 5 is controlled on the basis of the obtained information regarding the number of unused consumable elements 4 of the carrier band 3 remaining in the supply thereof. In this manner, it is possible to keep the time required for providing a consumable element 4 constant, regardless of the thickness of the reel 6.

The information regarding the supply of unused consumable elements 4 of the carrier band 3, which is obtained from the angle of rotation and from an associated band transport length by which the carrier band 3 is moved with a rotation of the reel 6 about said angle of rotation, can be stored in a counter. When a consumable element 4 is used, the counter status is then adjusted by one. With the actuation of the wind-up device 5, a control unit, not shown, can then assume that this information is probably correct and, if necessary, can correct it on the basis of a measurement of band travel speed.

A test element 4, as is illustrated in FIG. 2, is usually less flexible than the carrier band 3. Therefore a used consumable element 4 can lead to an imbalance in the reel 6. Because of such an imbalance in the reel 6, the band transport length is dependent not only on the size of a rotational angle, but also upon the rotational angle position of the reel 6. Therefore, because the band transport length is detected on the basis of the rotational angle position of the reel 6, a value for the imbalance in the reel 6 can be determined. On the basis of this value, a fresh carrier band 3, which carries unused consumable elements 4, can be distinguished from a carrier band 3 which has already been partially wound up, and which carries at least one used consumable element 4. In this manner, the replacement of a band cartridge 1 can be detected by the hand-held device 2 and can be taken into consideration in the actuation of the wind-up device 5.

Figure 4:
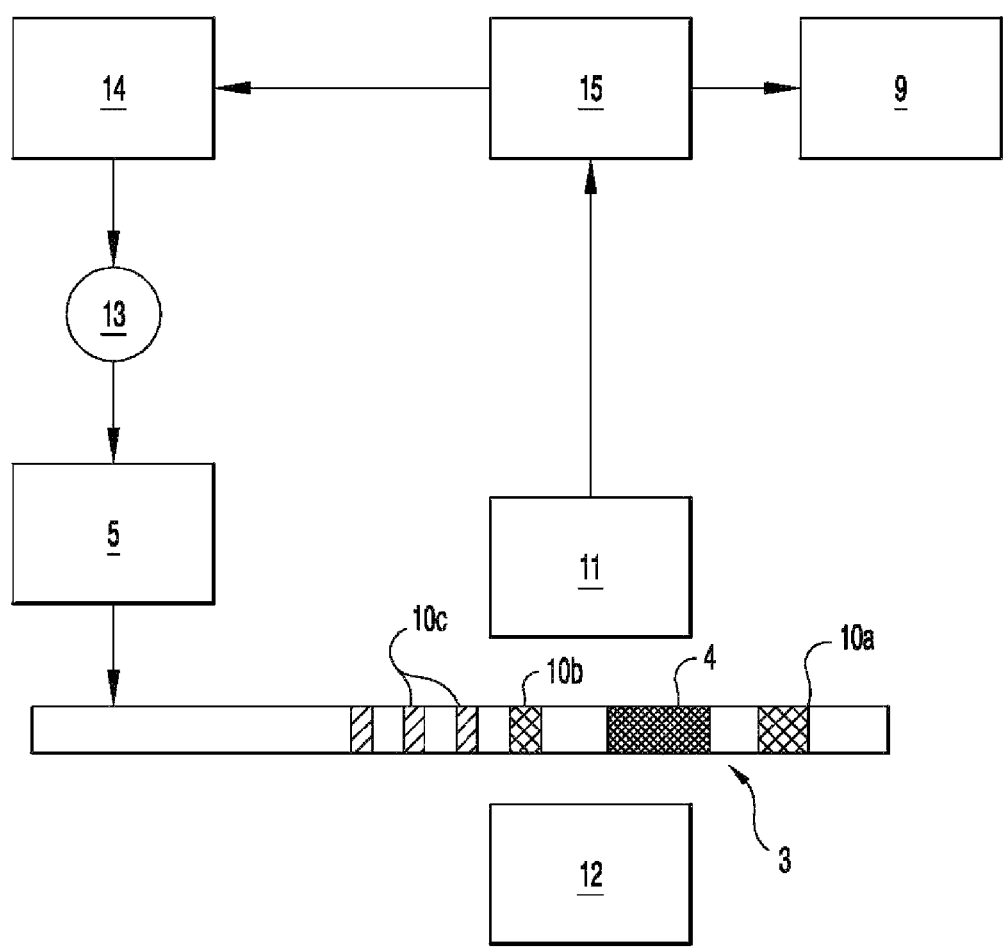
FIG. 4 shows a block diagram of an embodiment of the system for testing a sample of bodily fluid.

As illustrated in the block diagram of FIG. 4, an embodiment of a system for testing a bodily fluid can include a carrier band 3 with consumable elements 4 in the form of test elements. The carrier band 3 also may include various markings, 10*a*, 10*b*, 10*c*, which can be detected by an optical sensor 11. A wind-up device 5 for advancing the carrier band 3 is driven by an electric motor 13, which is controlled by a control device 14 that receives input from an analysis unit 15. The analysis unit 15 being supplied with information regarding the angle of rotation via the rotation of the electric motor 13 and the band transport length via the optical sensor 11 and a corresponding light source 12 disposed on different sides of the carrier band 3. The analysis unit 15 also can provide information regarding a supply of yet unused consumable elements of the carrier band to a user via an electronic display 9.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A system for determining a number of unused consumable elements for testing a sample of bodily fluid, the system comprising:
    a carrier band carrying a plurality of consumable elements, wherein one end of the carrier band is attached to a wind-up device for winding the carrier band with used consumable elements onto a reel for band transport;
    an analysis unit programmed to determine the number of yet unused consumable elements of the carrier band from an angle of rotation of the reel and band transport length by which the carrier band is moved with a rotation of the reel about the angle of rotation; and
    a display for displaying the number of yet unused consumable elements of the carrier band.

2. The system according to claim 1, further comprising an optical sensor, and wherein the carrier band includes markings disposed at regular intervals that are detectable by the optical sensor, and the analysis unit is configured to provide an indication of the band transport length based upon detection of the markings by the optical sensor.

3. The system according to claim 2, wherein the carrier band further includes stop markings, and the analysis unit is configured to stop the wind-up device based upon detection of the stop markings by the optical sensor.

4. The system according to claim 2, further comprising a light source for illuminating a measuring spot on the carrier band, which spot is detected by the sensor.

5. The system according claim 1, further comprising an electric motor configured for driving the wind-up device.

6. The system according to claim 1, wherein the analysis unit is configured to control the wind-up device based upon the obtained information regarding the supply of unused consumable elements of the carrier band.

7. The system according to claim 1, wherein the consumable elements include one or both of test elements and lancets.

8. The system according to claim 1, wherein the display is an electrical display.

9. The system according to claim 1, wherein the analysis unit is configured to control the rotational speed of the wind-up device for band transport, and wherein the rotational speed is reduced as the number of unused consumable elements of the carrier band decreases.

10. The system according to claim 1, further comprising a control device for controlling a band travel speed at which a consumable element is being provided, to a target value that is independent of the thickness of the reel.

11. The system according to claim 1, further comprising a counter status being displayed on the display, and the analysis unit being configured to control the counter status by one when a consumable element is used.

12. The system according to claim 1, wherein the carrier band is contained in a band cartridge.

13. A system for determining a number of unused consumable elements for testing a sample of bodily fluid, the system comprising:
    a carrier band carrying a plurality of consumable elements, one end of the carrier band being attached to a wind-up device for winding the carrier band with used consumable elements onto a reel for band transport;
    an analysis unit programmed to determine the number of yet unused consumable elements of the carrier band from a rotational angle position of the reel from which a value for an imbalance of the reel is determined, wherein a fresh carrier band carrying only unused consumable elements is distinguishable on the basis of the value for the imbalance of the reel from a carrier band which has already been partially wound up and which carries at least one used consumable element; and
    a display.

14. The system according to claim 13, further comprising a counter status being displayed on the display, and the analysis unit being configured to control the counter status by one when a consumable element is used.

15. The system according to claim 13, wherein the carrier band is contained in a band cartridge.

16. A method for monitoring a number of unused consumable elements carried by a carrier band, comprising:

using at least one consumable element;

winding the carrier band having used consumable elements onto a reel;

determining an angle of rotation of the reel and a band transport length by which the carrier band is moved during the winding step;

obtaining the number of unused consumable elements of the carrier band from the angle of rotation and the band transport length; and providing the number of unused consumable elements remaining on the carrier band.

* * * * *